United States Patent [19]

Inoue et al.

[11] Patent Number: 5,947,949
[45] Date of Patent: Sep. 7, 1999

[54] DISPOSABLE DIAPER

[75] Inventors: Yasushi Inoue; Yasushi Sayama, both of Kagawa-ken; Shunsuke Fujino, Ehime-ken, all of Japan

[73] Assignee: Uni-Charm Corporation, Ehime-ken, Japan

[21] Appl. No.: 08/905,342

[22] Filed: Aug. 4, 1997

[30] Foreign Application Priority Data

Aug. 7, 1996 [JP] Japan ................................. 8-208591

[51] Int. Cl.[6] .................................................. A61F 13/15
[52] U.S. Cl. ................................... 604/385.2; 604/385.1
[58] Field of Search ............................ 604/385.1, 385.2, 604/387

[56] References Cited

U.S. PATENT DOCUMENTS

| | | |
|---|---|---|
| 4,695,278 | 9/1987 | Lawson . |
| 4,816,025 | 3/1989 | Foreman . |
| 5,026,364 | 6/1991 | Robertson . |
| 5,246,432 | 9/1993 | Suzuki et al. ................. 604/385.2 |
| 5,624,424 | 4/1997 | Saisaka et al. ................ 604/385.2 |
| 5,649,919 | 7/1997 | Ruessler et al. ............... 604/385.2 |

FOREIGN PATENT DOCUMENTS

| | | |
|---|---|---|
| 4224750 | 8/1992 | Japan . |
| 4295356 | 10/1992 | Japan . |
| 5003891 | 1/1993 | Japan ................. 604/385.1 |
| 5042180 | 2/1993 | Japan ................. 604/385.1 |
| 5042181 | 2/1993 | Japan ................. 604/385.1 |

Primary Examiner—John G. Weiss
Assistant Examiner—K. M. Reichle
Attorney, Agent, or Firm—Lowe Hauptman Gopstein Gilman & Berner

[57] ABSTRACT

A disposable diaper includes a liquid-permeable topsheet, a liquid-impermeable backsheet and an absorbent core therebetween. A pair of contractible leg-gasket cuffs extend outward beyond transversely opposite side edges of the absorbent core and a pair of contractible barrier cuffs extend adjacent the side edges of the absorbent core and are biased to rise from an upper surface of the top sheet above the absorbent core. Each of the barrier cuffs is made of a nonwoven fabric and each of the leg-gasket cuffs is formed with a portion of the nonwoven fabric extending outward and a portion of the backsheet extending outward beyond the side edge of the absorbent core and bonded onto the extending portion of the nonwoven fabric. A reinforcing sheet is bonded to an upper surface of each of the leg-gasket cuffs along its outer side edge in order to enhance a tensile strength of the leg-gasket cuff. The reinforcing sheet is made of a nonwoven fabric.

5 Claims, 2 Drawing Sheets

1

DISPOSABLE DIAPER

BACKGROUND ART OF THE INVENTION

This invention relates generally to a disposable diaper being elastically stretchable around a wearer's legs.

U.S. Pat. No. 4,695,278 discloses a disposable diaper provided with a pair of elastically stretchable leg-gasket cuffs and a pair of elastically stretchable barrier cuffs extending from a crotch region into front and rear waist regions of the diaper. In this known diaper art, the gasket cuffs are formed by bonding together respective portions of a liquid-permeable topsheet and a liquid-impermeable backsheet covering upper and lower surfaces of a liquid-absorbent core, respectively, which extend outward beyond transversely opposite side edges of the absorbent core. A portion of each gasket cuff lying in the crotch region is provided with elastic members disposed between the topsheet and the backsheet and bonded to an inner surface of at least one of these sheets in longitudinally stretched conditions. Each of the barrier cuffs is formed by bonding a narrow piece of sheet extending longitudinally of the diaper along its portion extending inboard of the elastic members for the leg-gasket cuff to an upper surface of the topsheet or by curving upward in an inverted U-shape the portion of the topsheet extending outward beyond the side edge of the absorbent core inboard of the elastic members for the leg-gasket cuff.

In the above-mentioned diaper, each of the leg-gasket cuffs is formed by bonding the liquid-permeable topsheet to the liquid-impermeable backsheet made of plastic film. The gasket cuff made of the liquid-permeable topsheet alone would provide a comfortable touch but would be of insufficient strength. In addition, it would be difficult for such gasket cuff to prevent body fluids from leaking around a wearer's leg. The gasket cuff made of the liquid-impermeable backsheet in the form of plastic film alone, on the other hand, would have insufficient air-permeability even though it may be possible for such a gasket cuff to alleviate leakage of body fluids. The gasket cuff made of the topsheet and the backsheet bonded together certainly eliminates many of these problems but insufficient air-permeability remains a problem to be solved.

SUMMARY OF THE INVENTION

In view of the problem described above, it is a principal object of the invention to provide a disposable diaper including a pair of air-permeable leg gasket cuffs.

The object set forth above is achieved, according to the invention, by a disposable diaper comprising a liquid-permeable topsheet, a liquid-impermeable backsheet and a liquid-absorbent core disposed therebetween which form a front waist region, a rear waist region and a crotch region extending therebetween. A pair of leg-gasket cuffs extend outward beyond transversely opposite side edges of the absorbent core in at least the crotch region so as to have an elastic stretchability in a longitudinal direction of the diaper. A pair of barrier cuffs extend in the longitudinal direction adjacent the side edges of the absorbent core and are normally biased to rise from an upper surface of the topsheet. Transversely opposite side edges of the topsheet lie adjacent the transversely opposite side edges of the absorbent core, respectively. Transversely opposite side edges of the backsheet extend outward beyond the transversely opposite side edges of the absorbent core and lie outboard of the side edges of the topsheet, respectively. Each of the barrier cuffs is made of an air-permeable nonwoven fabric and has a distal edge lying adjacent the associated side edge of the absorbent core and a proximal portion lying outboard of the distal edge and bonded to an upper surface of said topsheet. The nonwoven fabric extends outward beyond the proximal portion so as to form one of the leg-gasket cuffs having a lower surface thereof adjacent the proximal portion bonded to an upper surface of the backsheet along the associated side edge of the core. Each of the leg-gasket cuffs if provided along an outer side edge thereof spaced apart from the associated proximal portion of the barrier cuff with a reinforcing sheet which both extends above and is bonded to an upper surface of each of the leg-gasket cuffs to enhance a tensile strength of each of the leg-gasket cuffs. In a region defined between the proximal portion of each of the barrier cuffs and an inner side edge of each of the reinforcing sheets, elastically stretchable members are disposed between the leg-gasket cuff and the backsheet and bonded to at least one of the leg-gasket cuff along the lower surface thereof or the backsheet along the upper surface thereof in longitudinally stretched conditions thereof so as to provide the leg-gasket cuff with elastic stretchability.

With the disposable diaper according to the invention, the barrier cuffs as well as the leg-gasket cuffs adapted to contact with a wearer's soft skin are formed by a thin and soft nonwoven fabric in order to avoid undesirable irritation of the skin The problem that the leg-gasket cuffs formed by such nonwoven fabric might be readily torn in the course of handling the diaper is avoided since the tensile strength of the leg-gasket cuffs are sufficiently enhanced by the reinforcing sheets.

Both the barrier cuffs and the leg-gasket cuffs are made of an air-permeable, and preferably also a liquid-impermeable, nonwoven fabric that serve to prevent the diaper, particularly in the crotch region, from becoming stuffy.

The elastic members for the leg-openings are partially covered with the nonwoven fabric and the backsheet so as to prevent the elastic stretchability thereof from being significantly reduced. A desired fitting of the leg-gasket cuffs around a wearer's legs is thereby maintained for prevention of body fluid leakage.

Other and further objects, features and advantages of the invention will appear more fully from the following description.

MODES FOR CARRYING OUT THE INVENTION

Figure 1:
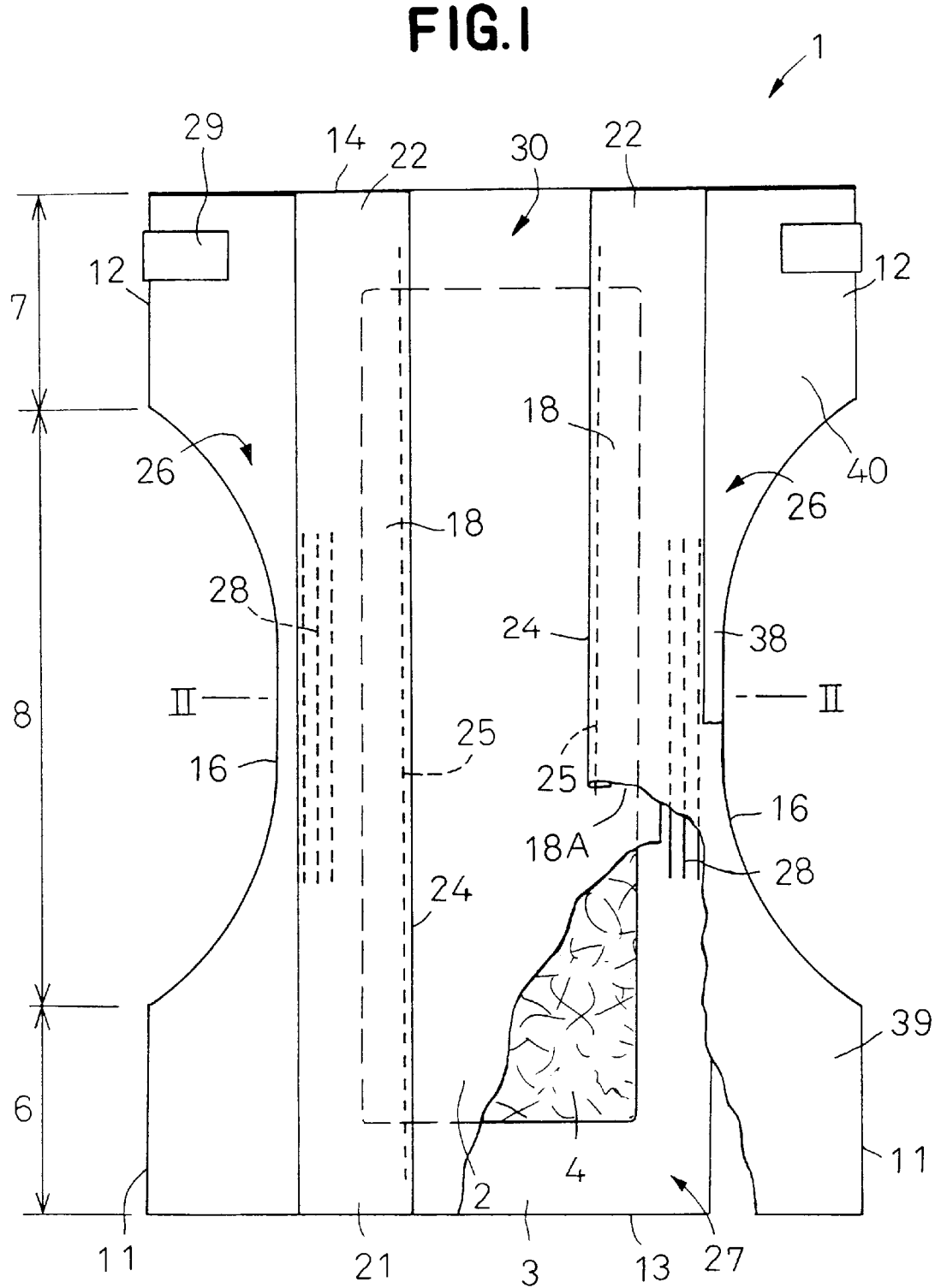
FIG. 1 is a plan view showing an embodiment of a disposable diaper according to the invention as partially broken away.

A disposable diaper 1 shown by FIG. 1 in a plan view as partially broken away comprises a liquid-permeable topsheet 2, a liquid-impermeable backsheet 3 and a liquid-absorbent core 4 disposed between sheets 2, 3. These components form a front waist region 6, a rear waist region 7 and a crotch region 8 extending between regions 6, 7. The front and rear waist regions 6, 7 have their transversely opposite side edges 11, 11 and 12, 12 extending in parallel to each other, respectively, and their longitudinal ends 13, 14 extending orthogonal to the side edges. Transversely opposite side edges of the crotch region 8 respectively define inwardly curved side edges 16 adapted to form respective leg-openings. The diaper 1 is formed on its inner surface with a pair of barrier cuffs 18 extending longitudinally of the diaper 1. Each of the barrier cuffs 18 is bonded at its longitudinally opposite ends 21, 22 and along its outer proximal portion 33 (FIG. 2) an inner surface of the diaper 1, leaving its inner side edge 24 free so as to form a pocket 18A, as will be described in more detail later, which is adapted to open toward a centerline (not shown) dividing the diaper 1 into left and right halves. The inner side edge 24 is provided with an elastic member 25 in their longitudinally stretched conditions. FIG. 1 shows this barrier cuff 18 as flattened on an upper surface of the topsheet 2 to close the pocket 18A.

The absorbent core 4 is rectangular or hourglass-shaped. A pair of leg-gasket cuffs 26 adapted to surround a wearer's legs are provided outboard of the core's transversely opposite side edges. There are provided outboard of longitudinally opposite ends of the absorbent core 4 end-flaps 27, 30, respectively, adapted to surround a wearer's front and rear waist lines. Each of the leg-gasket cuffs 26 is provided along its intermediate zone with a plurality of elastic members 28 attached thereto in their longitudinally stretched conditions. The rear waist region 7 is provided on opposite side edges thereof with a pair of tape fasteners 29.

Figure 2:
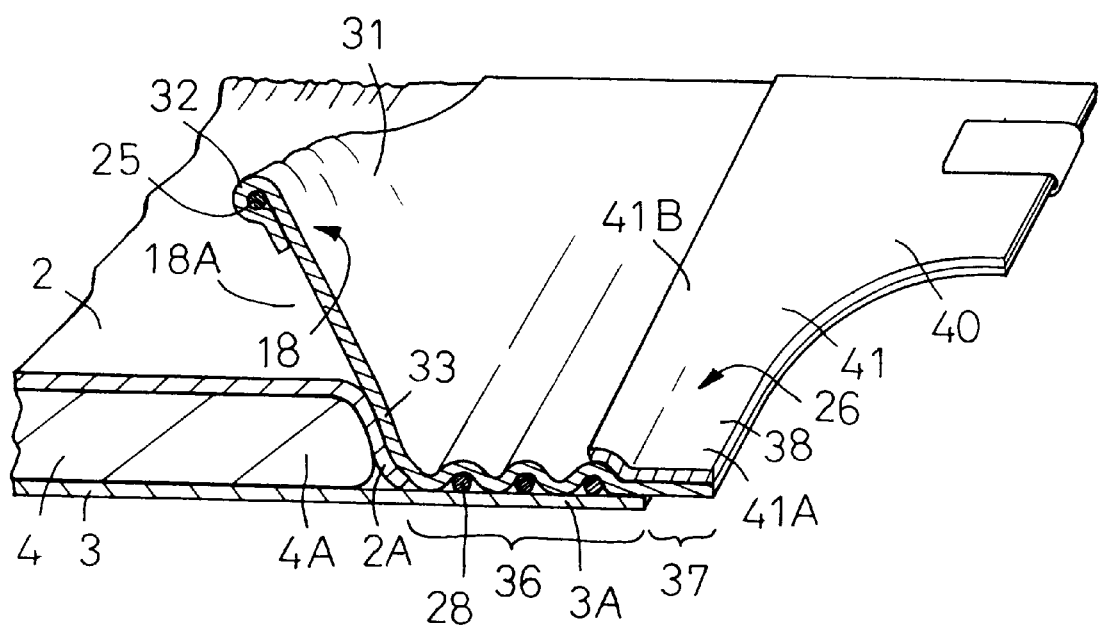
FIG. 2 is a fragmentary perspective view showing a section of the diaper taken along line II—II in FIG. 1.

FIG. 2 is a fragmentary perspective view showing the diaper 1 partially in a section taken along line II—II in FIG. 1 with the barrier cuff 18 rising from the inner surface of the diaper 1. The topsheet 2 has its side edge 2A terminating at the side edge 4A of the absorbent core 4. The backsheet 3 has its side edge 3A extending outward beyond the side edge 2A of the topsheet 2. The barrier cuff 18 is formed by a sheet member 31 extending outward transversely of the diaper 1. The barrier cuff 18 has distal edge 24 and a proximal portion 33 bonded to the side edge 2A of the topsheet 2, and cooperates with the topsheet 2 so as to form the pocket 18A. The sheet member 31 is folded back to its inner surface and thereby wraps an elastic member 25 which is, in turn, bonded to an inner surface of the barrier cuff 18 by means of adhesive (not shown). With the diaper 1 curved longitudinally with its inner surface inside, the elastic member 25 contracts so that the barrier cuff 18 rises from the inner surface of the diaper 1 and the pocket 18A is fully opened inwardly of the diaper 1.

A portion 36 of the sheet member 31 extending outward from the proximal portion 33 is bonded to an upper surface of the backsheet 3 along the side edge 3A and the sheet member 31 includes a portion 37 extending further from the portion 36. The portions 36, 37 of the sheet member 31 form the side flap 26 which comprises a relatively narrow leg-gasket cuff 38 defined in the crotch region 8 and a pair of relatively wide waist-flaps 38, 40 (See FIG. 1 also). A plurality of elastic members 28 extending longitudinally of the diaper 1 are arranged between the portion 36 of the sheet member 31 and the side edge 3A of the backsheet 3 and bonded to an inner surface of at least one of the portion 36 and the side edge 3A in their longitudinally stretched conditions by means of hot melt adhesive (not shown). The portion 37 of the sheet member 31 is provided with a reinforcing sheet 41 bonded to an upper surface thereof in order to reinforce a tensile strength of the sheet member 31. An outer side edge 41A of the reinforcing sheet 41 conforms with the outer side edge of the sheet member 31 and an inner side edge 41B may extend inward to overlap the side edge 3A of the backsheet 3 or to overlap a part of the plural elastic members 28 but not extend to the proximal portion 33 of the barrier cuff 18 so as to cover all the plural elastic members 28. It is essential to leave at least one of the elastic members 2B not covered with the reinforcing sheet 41B in a region defined between the inner side edge 41B and the proximal edge 33.

In the diaper constructed as has been described hereinabove, the topsheet 2 may be formed by a liquid-permeable, more preferably, liquid-permeable and hydrophobic sheet material made of nonwoven fabric or perforated plastic film. The backsheet 3 may be formed by a liquid-impermeable, more preferably, liquid-impermeable but air-permeable sheet material made of plastic film or the like. The sheet member 31 may be formed by an air-permeable nonwoven fabric, more preferably, liquid-impermeable but air-permeable nonwoven fabric. Such nonwoven fabric may be an air-permeable but liquid-impermeable spun bonded nonwoven fabric, a spun laced nonwoven fabric or a melt blown nonwoven fabric having a basis weight of 5–50 g/m$^2$ and a water resistance of 10 cm or higher as measured according to the testing method A of JIS-L1092. The reinforcing sheet 41 may be formed by an air-permeable, more preferably, air-permeable but liquid-impermeable nonwoven fabric having a basis weight of 20–150 g/m$^2$. Bonding of these sheet materials may be achieved by use of a suitable adhesive agent such as hot melt adhesive or, if the materials are thermally meltable, by welding techniques using heat embossing or ultrasonic treatment.

Having described our invention as related to the embodiment shown in the accompanying drawings, it is our intention that the invention be not limited by any of the details of description, unless otherwise specified, but rather be construed broadly within its spirit and scope as set out in the accompanying claims.

What is claimed is:

1. A disposable diaper comprising a liquid-permeable topsheet, a liquid-impermeable backsheet and a liquid-absorbent core disposed therebetween which form a front waist region, a rear waist region and a crotch region extending therebetween, a pair of leg-gasket cuffs extending outward beyond transversely opposite side edges of said absorbent core in at least said crotch region so as to have an elastic stretchability in a longitudinal direction of the diaper, and a pair of barrier cuffs extending in said longitudinal direction adjacent said side edges of said absorbent core and normally biased to rise from an upper surface of said topsheet, wherein:

transversely opposite side edges of said topsheet lie adjacent said transversely opposite side edges of said absorbent core, transversely opposite side edges of said backsheet extend outward beyond said transversely opposite side edges of said absorbent core and lie outboard of said side edges of said topsheet, respectively, each of said barrier cuffs is made of an air-permeable nonwoven fabric and has a distal edge lying adjacent the associated side edge of said absorbent core and a proximal portion lying outboard of said distal edge and bonded to the upper surface of said topsheet, said nonwoven fabric extends outward beyond said proximal portion so as to form one of said leg-gasket cuffs having a lower surface thereof adjacent said proximal portion bonded to an upper surface of said backsheet along the associated side edge of said core, each of said leg-gasket cuffs is provided along an outer side edge thereof spaced apart from the associated proximal portion of said barrier cuff with a reinforcing sheet which both extends above and is bonded to an upper surface of each of said leg gasket cuffs to enhance a tensile strength of each of said leg-gasket cuffs, and p1 in a region defined between said proximal portion of each of said barrier cuffs and an inner side edge of each of said reinforcing sheets, elastically stretchable members are disposed between said leg-gasket cuff and said backsheet and bonded to at least one of said leg-gasket cuff along said lower surface thereof or said backsheet along said upper surface thereof in a longitudinally stretched conditions thereof so as to provide said leg-gasket cuff with said elastic stretchability.

2. The disposable diaper according to claim 1, wherein said nonwoven fabric is air-permeable but liquid-impermeable.

3. The disposable diaper according to claim 2, wherein said nonwoven fabric has a basis weight of 5–50 g/m$^2$.

4. The disposable diaper according claim 1, wherein said reinforcing sheet is made of a nonwoven fabric which is air-permeable but liquid-impermeable.

5. The disposable diaper according to claim 4, wherein said nonwoven fabric has a basis weight of 20–150 g/m$^2$.

* * * * *